(12) United States Patent
Matsuyama

(10) Patent No.: US 6,485,760 B2
(45) Date of Patent: *Nov. 26, 2002

(54) METHOD FOR INHIBITING INCREASE OF BLOOD SUGAR LEVEL OR LOWERING BLOOD SUGAR LEVEL WITH A LAGERSTROEMIA EXTRACT

(76) Inventor: Futoshi Matsuyama, c/o Use•Techno Corporation, 2101 Osada Ichinotani, Fukuchiyama-shi, Kyoto 620-0848 (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/437,342

(22) Filed: Nov. 10, 1999

(65) Prior Publication Data

US 2001/0006941 A1 Jul. 5, 2001

(30) Foreign Application Priority Data

Dec. 9, 1998 (JP) ............................................. 10-349667

(51) Int. Cl.⁷ ........................ A61K 35/78; A61K 31/015
(52) U.S. Cl. ........................ 424/775; 514/693; 514/763
(58) Field of Search ............................. 424/195.1, 775; 514/693, 766, 763; 536/1.11

(56) References Cited

U.S. PATENT DOCUMENTS 4,544,550 A * 10/1985 Rodolfo ...................... 424/127

FOREIGN PATENT DOCUMENTS

| JP | 5310587 | 11/1993 |
| WO | 05310587 | * 11/1993 |
| WO | 07228538 | * 8/1995 |

OTHER PUBLICATIONS

Chikage Murakami, et al., Screening of Plant Constituents for Effect . . . , Chem. Pharm. Bull., 41(12), pp. 2129–2131. (Sep. 1993).

Yamahara, Johji, et al.: "Biologically active principles of crude drugs . . . " Yakugaku Zasshi, vol. 101, No. 1, 1981, pp. 86–90.

DeTommasi, Nunziatina, et al.: "Hypoglycemic effects of sesquiterpen glycosides and polyhydroxylated triterpenoids of eriobotyra japonica", Planta Med., vol. 57, No. 5, 1991, pp. 414–416.

Murakami, Chikage, et al.: "Screening of plant constituents for effect on glucose transport activity in Ehrlich ascites tumor cells" Chem. Pharm. Bull., vol. 41, No. 12, 1993, pp. 2129–2131.

Database WPI, Section Ch, Week 199401, Derwent Publications Ltd., London, GB; 1994–002236, Nov. 22, 1993, Abstract only.

Mishra et al. Hypoglycaemic activity of leaves of Lagerstroemia speciosa (L) Pers. Indian Journal of Pharmacology 22, pp. 174–176. (1990). No month.*

* cited by examiner

Primary Examiner—John S. Brusca
Assistant Examiner—Marjorie A. Moran

(57) ABSTRACT

A composition for inhibiting an increase in, or lowering, a blood sugar level, which comprises, as a main component, a concentrate of a hot water or alcohol extract of leaves of Lagerstroemia Speciosa, Linn. or Pers. and has an corosolic acid content of 0.01 to 15 mg per 100 mg of the concentrate, and a method of inhibiting an increase in, or lowering, a blood sugar level by oral administration of the composition.

17 Claims, No Drawings

METHOD FOR INHIBITING INCREASE OF BLOOD SUGAR LEVEL OR LOWERING BLOOD SUGAR LEVEL WITH A LAGERSTROEMIA EXTRACT

DETAILED DESCRIPTION OF THE INVENTION

1. Field of the Invention

The present invention relates to a composition for inhibiting an increase of a blood sugar level or lowering a blood sugar level. More specifically, it relates to a composition for inhibiting an increase of a blood sugar level or lowering a blood sugar level, which composition contains extract components from Lagerstroemia Speciosa, Linn. or Pers. as a main component and has a specific content of corosolic acid.

2. Prior Art of the Invention

Lagerstroemia Speciosa, Linn. or Pers. comes under the loosestrife family of Myrtales and is generally called "queen's crape myrtle" as well, and it occurs widely in south east Asian areas including the Philippines, India, Malaysia, southern China and Australia. In the Philippines in particular, dry leaves and flowers of Lagerstroemia Speciosa, Linn. or Pers. are decoted and taken as a drink. This drink is also well known as a folk medicine against diabetes.

Leaves of Lagerstroemia Speciosa, Linn. or Pers. have received attention and an extract thereof has been analyzed for obtaining some components. It has been accordingly reported that corosolic acid is contained as one of the components and that the corosolic acid has been studied for its activity by using Ehrlich Ascites Tumour Cells to show that it is a substance which activates the mobility of grape sugar [Chem. Pharm. Bull. 41(12) 2129–2131 (1993)].

The above report is concerned with results of in vitro experiments and merely suggests results of first-stage discrimination test of anti-diabetes activities of corosolic acid.

JP-A-5-310587 discloses an anti-diabetes preparation containing, as an ingredient, a concentrated dry substance (Lagerstroemia Speciosa, Linn. or Pers. powder extract) obtained by extracting leaves of Lagerstroemia Speciosa, Linn. or Pers. in hot water or an organic solvent. The above preparation is an easily prepared and high-safety anti-diabetes preparation produced by taking out a water-soluble fraction and a lipid-soluble fraction from an extract of leaves of Lagerstroemia Speciosa, Linn. or Pers. and adjusting it to a dry extract. The above publication discloses a preferred embodiment in which the powder extract is diluted, e.g., in a concentration of 2% and taken as a drink, and the anti-diabetes activity thereof is confirmed by an animal experiment using mice diseased with diabetes.

As already described, dry leaves of Lagerstroemia Speciosa, Linn. or Pers. have been used as having an effect on the therapy of diabetes in folk medicine. However, it is not clearly known what component(s) of the leaves of Lagerstroemia Speciosa, Linn. or Pers. has/have human anti-diabetes activity. It is known that corosolic acid is contained as one component, while the activity thereof is a mere result of a study of the function to activate the mobility of grape sugar in an in vitro experiment using cells.

Further, there has been no specific clinical knowledge of component(s) of the extract of leaves of Lagerstroemia Speciosa, Linn. or Pers. which has/have activity in the therapy of human diabetes. Moreover, there has been found no knowledge obtained by studying a relationship between component(s) of the extract of leaves of Lagerstroemia Speciosa, Linn. or Pers. and an increase in a human blood sugar level.

The present inventor has therefore studied a relationship between component(s) of an extract of leaves of Lagerstroemia Speciosa, Linn. or Pers. and an increase or inhibition of an increase in human blood sugar level on the basis of clinical tests. When a composition which was a concentrated extract of leaves of Lagerstroemia Speciosa, Linn. or Pers. and which had a specific content of corosolic acid was administered to mild-case diabetes patients who had a fasting blood sugar level of slightly higher than approximately 110 mg/dl and who were insulin-non-dependent, it was found that an increase in blood sugar level was inhibited and that the blood sugar levels decreased on average.

According to studies by the present inventors, it has been also found that the composition which had a specific content of corosolic acid can be obtained by extracting, concentration and drying leaves of Lagerstroemia Speciosa, Linn. or Pers., under a specific condition.

Means to Solve the Problems

According to the present invention, therefore, there is provided a composition for inhibiting an increase in, or lowering, a blood sugar level, which comprises, as a main component, a concentrate of a hot water or alcohol extract of leaves of Lagerstroemia Speciosa, Linn. or Pers. and has a corosolic acid content of 0.01 to 15 mg per 100 mg of the concentrate.

According to the present invention, further, there is provided a method of inhibiting an increase in a blood sugar level, which comprises orally administering the above composition to a patient who is expected to suffer an increase in blood sugar level from a normal blood sugar level.

Further, according to the present invention, there is provided a method of lowering a blood sugar level to a normal level, which comprises orally administering the above composition to a mild-case diabetes patient having a blood sugar level higher than a normal level to some extent or a serious diabetes patient having a high blood sugar level.

The present invention will be explained more specifically hereinafter.

Corosolic acid is one of triterpenoids having the following structural formula.

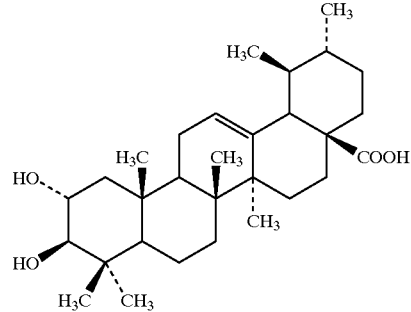

It is considered that the activity of the composition of the present invention in inhibiting an increase in, or lowering, a human blood sugar level is caused by the interaction of a specific content of corosolic acid in the concentrate and extracted components of leaves of Lagerstroemia Speciosa, Linn. or Pers.

Leaves of Lagerstroemia Speciosa, Linn. or Pers. used as a raw material for the composition of the present invention refer to green leaves of Lagerstroemia Speciosa, Linn. or Pers. which occurs in the Philippines or some other areas or a dry product prepared by drying the same. The green leaves may be dried by leaving it in atmosphere, by air-drying or by forcible drying. Preferably, the drying is carried out by so-called toasted-drying until the leaves have a water content of 20% by weight or less, preferably 10% by weight or less, for preventing the growth of microorganisms and attaining storage stability.

Green leaves of Lagerstroemia Speciosa, Linn. or Pers. may be extracted as they are, while it is desirable to pulverize the dry leaves or cut them into pieces before the extraction.

The method and condition of extracting leaves of Lagerstroemia Speciosa, Linn. or Pers. in hot water or an alcohol and concentrating the extract are not specially limited, while there should be employed a method and a condition under which a resultant concentrate has a specific content of corosolic acid. That is, the concentrate preferably has a corosolic acid content of 0.01 to 15 mg per 100 mg of the concentrate (dry solid substance). The corosolic acid content per 100 mg of the concentrate is preferably 0.1 to 15 mg, more preferably 0.2 to 12 mg, particularly preferably 0.5 to 10 mg.

In the composition of the present invention, those components of the leaves of Lagerstroemia Speciosa, Linn. or Pers. which are other than corosolic acid also have an effect on the activity, and it is required to take account of components to be extracted and a concentrating method and condition with regard to the other components. A preferred embodiment of a proper method and a proper condition will be apparent from an explanation to be given later.

Method 1

In this method, a pulverization product of dry leaves of Lagerstroemia Speciosa, Linn. or Pers. (raw material) added to ethanol or an ethanol aqueous solution (ethanol content 50 to 80% by weight) in an amount 5 to 20 times, preferably 8 to 10 times the weight of the raw material, and the mixture is refluxed under heat at a temperature between room temperature and 90° C., preferably approximately between 50° C. and 80° C., for 30 minutes to 2 hours. The above extraction is repeated twice or three times. The resultant extract may be decolorized as required by adding 5 to 10% by weight, based on the raw material, of activated carbon. The decolorization is useful for expanding the use range of the composition of the present invention to foods, and the like. Then, the extract is filtered and concentrated at a temperature of 60° C. or lower under reduced pressure to obtain a solid, and the solid is dried at a temperature between 50° C. and 70° C. under reduced pressure (higher reduction rate than that during the concentration). The thus-obtained solid is pulverized to obtain a powdery concentrate. The concentrate obtained by the above method has a specific content of corosolic acid and contains an effective amount of other components as well.

Method 2

This method is an extraction method using methanol or a methanol aqueous solution. In this method, the extraction is carried out in methanol or a methanol aqueous solution (methanol content 50 to 90% by weight) in an amount 3 to 20 times the weight of the raw material. The extraction procedure is preferably carried out at a temperature between room temperature and 65° C. for 30 minutes to 2 hours. The number of times of the extraction procedure is not limited to once, and the extraction procedure may be carried out twice or more. The obtained extract is decolorized as required, and concentrated under the same conditions as those in the above method 1, whereby a solid can be obtained.

Method 3

This method 3 is an extraction method using hot water. There is used hot water in an amount 3 to 20 times the weight of the raw material, and the extraction is carried out at a temperature between 50° C. and 90° C., preferably between 60° C. and 85° C., for 30 minutes to 2 hours. Desirably, the concentration and drying after the extraction are carried out for a relatively short period of time since active components may be sometimes deteriorated when the concentrate is maintained at a high temperature for a long period of time. For this reason, it is advantageous to carry out the concentration and the drying under reduced pressure.

The above-explained methods 1 to 3 have been described for explaining basic methods and conditions, and these methods may be altered and/or combined as required. For example, the method 1 and the method 2 may be combined. Of the above methods 1 to 3, the methods 1 and 2 are preferred, and the method 1 is particularly preferred. Function and effect of the composition of the present invention When used as a preparation for inhibiting an increase in, or lowering, the blood sugar level, the composition of the present invention has the following advantages.

(a) It has been reported that conventional oral preparations for the therapy of diabetes such as a sulfonyl urea preparation, a biguanide preparation, an insulin resistant amelioration preparation, etc., causes side effects such as hepatopathy, disorder of digestive organs, nausea, vomitting, etc., while the composition of the present invention is free of these side effects.

(b) The above conventional preparations for the therapy of diabetes end their effects when the administration thereof is discontinued, while the composition of the present invention continues to have an effect and has a continuing effect like traditional Chinese medicine since the blood sugar level does not increase when its administration is discontinued.

(c) The composition of the present invention does not cause a decrease in the blood sugar level when people having a normal blood sugar level takes it.

(d) It is considered that the above advantages of the composition of the present invention are exhibited since corosolic acid contained in leaves of Lagerstroemia Speciosa, Linn. or Pers. activates grape sugar transportation even if its concentration is very low.

It is considered that intensification of the grape sugar transportation activity of corosolic acid in "intaking of sugar" and "conversion of sugar to energy" is a function different from that of conventional preparations for the therapy of diabetes.

(e) It is also assumed that the composition of the present invention has another activity in inhibiting the digestion and absorption of glucide by preventing the function of typical digestive enzyme of glucide. It is considered that the above activity is caused by the interaction of corosolic acid and other component(s) in the concentrated extract of leaves of Lagerstroemia Speciosa, Linn. or Pers.

The composition of the present invention can therefore inhibit an increase in a blood sugar level by orally administering it to patients who are expected to suffer an increase in blood sugar level from a normal blood sugar level. The above oral administration can be continued for a long period of time, and even if the composition of the present invention is continuedly taken for a long period of time, the blood sugar level comes to be lower than a normal blood sugar level in no case. Further, the oral administration causes no or almost no other harms or side effects.

Further, when orally administered to diabetes patients, the composition of the present invention can lower their blood sugar level to a normal level. The composition of the present invention can work on any one of mild-case patients having a blood sugar level higher than a normal blood sugar level to some extent and serious patients having a considerably higher blood sugar level.

When the composition of the present invention is orally administered, desirably, the dosage of the concentrate having a corosolic acid content of 0.01 to 15 mg per kg of a human body weight per day is 50 mg to 1,000 mg, preferably 70 mg to 800 mg. Specifically, the oral administration is preferably separated to twice or three times a day. Desirably, further, the oral administration of the composition of the present invention is conducted continuedly for at least one month, preferably for at least three months.

The composition of the present invention may have the preparation form of a powder or granules, and it may also have the preparation form of a tablet such as pellets or an encapsulated preparation.

EXAMPLES

The present invention will be explained more specifically with reference to Examples hereinafter.

Example 1

(1) Preparation of Concentrate From Dry Leaves of Lagerstroemia Speciosa, Linn. or Pers.

1 Kg of dry leaves of Lagerstroemia Speciosa, Linn. or Pers. from the Philippines were cut, placed in 5 liters of a 80 wt % ethanol aqueous solution and extracted under reflux under heat (approximately 85° C.) for 1.5 hours. After the extraction, the leaves of Lagerstroemia Speciosa, Linn. or Pers. were separated by filtration, again placed a 80 wt % ethanol aqueous solution and extracted under reflux under heat (approximately 85° C.) for 1.5 hours. The leaves of Lagerstroemia Speciosa, Linn. or Pers. were separated by filtration. Extracts obtained by the first and second extraction procedures were combined, and 500 g of activated carbon was added to carry out decolorization. After the activated carbon was removed, ethanol and water were removed under reduced pressure at 60° C. to give a concentrate. Then, the concentrate was maintained further under reduced pressure at 60° C. to give a dry solid. The solid was pulverized to give 150 g of a powdery concentrate.

(2) Analysis of Corosolic Acid

One gram of the powdery concentrate obtained in the above (1) was dissolved in 10 ml of methanol and analyzed by high-performance liquid chromatography (HPLC) to show a corosolic acid content of 30 mg in the above concentrate (corresponding to 3 mg of corosolic acid per 100 mg of the concentrate).

(3) Preparation of Tablet

The powdery concentrate obtained in the above (1) was used to prepare tablets containing the following components for a clinical test.

| Components | % by weight |
|---|---|
| Powdery concentrate | 50 |
| Dietary fiber*[1] | 20 |
| Sucrose fatty acid ester | 3 |
| Lactose | 22 |
| Hardened oil*[2] | 5 |
| | 100 |

*[1]Crystalline cellulose
*[2]Hardened rapeseed oil

The above components were homogeneously mixed and prepared into tablets having a weight of 250 mg each ("tablets A" hereinafter) with a tablet machine.

Further, tablets containing no powdery concentrate ("tablets B" hereinafter) which were indistinguishable from the tablets A were prepared in the same manner as above except that diluents alone were used without the powdery concentrate.

(4) Clinical Test

Twenty-two mild-case insulin non-dependent patients having a a fasting blood sugar level of approximately 100 to 210 mg/dl were classified into two groups.

The Group I (11 patients of one group) were allowed to take three tablets A each time after meals three times a day with a cup of water for 4 weeks from the beginning of the first to the end of the fourth week, and the tablets B were administered under the same conditions for 4 weeks from the beginning of the fifth week.

On the other hand, the Group II (11 patients of the other group) were allowed to take three tablets B each time after meals three times a day with a cup of water for 4 weeks from the beginning of the first to the end of the fourth week, and the tablets A were administered under the same conditions for 4 weeks from the beginning of the fifth week.

In the beginning of the administration, after 4 weeks and after 8 weeks from the administration, bloods of the patients were sampled three times and studied for blood sugar levels. Table 1 shows the results.

TABLE 1

| | Beginning | | After 4 weeks | | After 8 weeks |
|---|---|---|---|---|---|
| Group I (11 patients) Average (mg/dl) | 169.1 | → tablet A | 132.8 | → tablet B | 143.4 |
| Group II (11 patients) Average (mg/dl) | 129 | → tablet B | 128 | → tablet A | 110 |

The tablets A were studied for a significant difference to show a Prob>(T) value of 0.0030 and that the tablets A had a high-degree significant difference in decreasing the blood sugar level.

What is claimed is:

1. A method of inhibiting an increase in blood sugar level in a human patient who is expected to suffer an increase in blood sugar level, which comprises orally administering to said patient an active ingredient containing concentrate consisting essentially of ethanol or ethanol aqueous solution extract of leaves of Langerstroemia Speciosa, Linn. or Pers., said concentrate having a corosolic acid content of 0.1 to 15 mg per 100 mg of the concentrate, said concentrate being administered at a dose of 50 mg to 1,000 mg per kg of body weight of said patient per day, which is effective to inhibit an increase in blood sugar level in said patient.

2. The method according to claim 1, which comprises administering the concentrate to said patient twice daily.

3. The method according to claim 1, which comprises administering the concentrate to said patient three times daily.

4. The method according to claim 1, which comprises administering the concentrate in the form of a tablet.

5. The method according to claim 1, which comprises administering the concentrate in the form of powder or granules.

6. The method according to claim 1, wherein said concentrate has a corosolic acid content of from 0.2 to 12 mg, per 100 mg of the concentrate.

7. The method according to claim 1, wherein said concentrate has a corosolic acid content of from 0.5 to 10 mg, per 100 mg of the concentrate.

8. The method according to claim 1, wherein the concentrate is orally administered at a dose of from 70 to 800 mg per kg of body weight.

9. A method of lowering blood sugar level to normal level in a human diabetes patient having a blood sugar level above normal blood sugar level, which comprises orally administering to said diabetes patient an active ingredient containing concentrate consisting essentially of ethanol or ethanol aqueous solution extract of leaves of Lagerstroemia Speciosa, Linn. or Pers., said concentrate having a corosolic acid content of 0.1 to 15 mg per 100 mg of the concentrate, said concentrate being administered at a dose of 50 mg to 1,000 mg per kg of body weight of said patient per day, which is effective to lower blood sugar level to a normal level in said diabetes patient.

10. The method according to claim 9, which comprises administering the concentrate to said patient twice daily.

11. The method according to claim 9, which comprises administering the concentrate to said patient three times daily.

12. The method according to claim 10, wherein said concentrate has a corosolic acid content of from 0.2 to 12 mg, per 100 mg of the concentrate.

13. The method according to claim 9 wherein said concentrate has a corosolic acid content of from 0.5 to 10 mg, per 100 mg of the concentrate.

14. The method according to claim 9, which comprises administering the concentrate in the form of a tablet.

15. The method according to claim 9, which comprises administering the concentrate in the form of powder or granules.

16. The method according to claim 1, wherein said ethanol aqueous solution contains 50 to 80% by weight of ethanol.

17. The method according to claim 9, wherein said ethanol aqueous solution contains 50 to 80% by weight of ethanol.

* * * * *